United States Patent [19]

Marks, Sr.

[11] Patent Number: 4,762,718

[45] Date of Patent: Aug. 9, 1988

[54] IN SITU INSECTICIDE

[75] Inventor: George B. Marks, Sr., Hudson, Wis.

[73] Assignee: Fearing Manufacturing Co., Inc., South St. Paul, Minn.

[21] Appl. No.: 42,618

[22] Filed: Apr. 20, 1987

Related U.S. Application Data

[63] Continuation of Ser. No. 632,957, Jul. 20, 1984, abandoned, which is a continuation-in-part of Ser. No. 544,319, Oct. 21, 1983, abandoned.

[51] Int. Cl.$^4$ ............................................. A01N 25/26
[52] U.S. Cl. ................................... 424/409; 424/405; 424/407; 424/417; 424/419; 514/944
[58] Field of Search ................ 514/531, 521; 424/405, 424/409, 417, 419; 514/944

[56] References Cited

U.S. PATENT DOCUMENTS

| | | | |
|---|---|---|---|
| 3,235,451 | 2/1966 | Odeneal | 167/42 |
| 4,283,415 | 8/1981 | Fuyama | 514/531 |
| 4,348,409 | 9/1982 | Holan et al. | 514/531 |
| 4,376,786 | 3/1983 | Maurer et al. | 514/531 |
| 4,390,715 | 6/1983 | Holan et al. | 514/531 |
| 4,404,223 | 9/1983 | Matthewson | 514/531 |
| 4,568,541 | 2/1986 | Dorn et al. | 424/81 |

FOREIGN PATENT DOCUMENTS

| | | |
|---|---|---|
| EP-A- | | |
| 0041654 | 5/1981 | European Pat. Off. |
| 170797 | 5/1976 | New Zealand . |
| 175136 | 5/1976 | New Zealand . |
| 177437 | 7/1977 | New Zealand . |
| 183390 | 10/1979 | New Zealand . |
| 188483 | 7/1981 | New Zealand . |
| 199904 | 5/1985 | New Zealand . |
| 1413491 | 3/1976 | United Kingdom . |
| 1511646 | 1/1978 | United Kingdom . |
| 1516113 | 1/1978 | United Kingdom . |
| 2002635A | 6/1979 | United Kingdom . |
| 2015877A | 1/1980 | United Kingdom . |
| 2031729A | 7/1980 | United Kingdom . |
| GB-A- | | |
| 2040684 | 9/1980 | United Kingdom . |

OTHER PUBLICATIONS

Equishield Gel, two pages (3/12/71).
New Zealand: *Queensland Country Life*, Sep. 25, 1980, p. 13.
NZVJ V 20, #9, Sep. 1972, p. 167.
NZVJ V 25, Dec. 1977, #12, p. 493-494.
New Zealand: *Farm Equipment News* article published Feb. 19, 1979, Issue 39.
U.S. Patent Abridgement 2213156, available in NZ Sep. 10, 1940.
U.S. Patent Abridgement 2089766 available NZ, Sep. 6, 1937.
Advances in Pesticide Science, Zurich 1978, pp.165-195.
Proceedings of the Entomological Society of Ontario, vol. 110, 1979.
C. A. Hall, The Effect of Cypermethrin (NRDC 149) for Treatment & Eradication of Sheep Louse Damalinia Ovis, Australian VJ, Oct. 1978.
NZVJ, V 28, #3, p. 39, 1980.
J. Agric. Food Chem., Moth-Proofing Wool and Wool-Blends with Permethrin, vol. 27, #2, 1979, p. 331.
A Comparison of New Synthetic Pyrethroids for the Industrial Insect-Proofing of Wool, J. Text. Inst., 1979, #2.

*Primary Examiner*—Thurman K. Page
*Attorney, Agent, or Firm*—Jacobson and Johnson

[57] ABSTRACT

A method and phase changing composition with an in situ insecticide for the killing of insects on animals over an extended period of time. The phase changing composition with an in situ insecticide comprises a film-former such as hydroxypropyl cellulose, ethyl cellulose and methyl cellulose, an insecticide and a rapidly evaporating solvent such as volatile alcohol. When the phase changing insecticide composition is applied to an animal, it leaves a liquid bead on the animal which penetrates and encapsulates a portion of the animal's body hairs. As the liquid solvent in the liquid bead evaporates, it forms a dry-to-the-touch gel bead that contains the in situ insecticide which is released from the gel bead over an extended period of time.

7 Claims, No Drawings

IN SITU INSECTICIDE

CROSS REFERENCE TO RELATED APPLICATIONS

This application is a continuation of application Ser. No. 632,957, filed July 20, 1984 now abandoned, which is a continuation-in-part of my U.S. application titled "IN SITU INSECTICIDE", U.S. Ser. No. 544,319 filed Oct. 21, 1983, now abandoned.

FIELD OF THE INVENTION

This invention relates generally to an in situ insecticide and, more specifically, to an in situ insecticide that is applied directly to a localized region of the animal yet provides protection from insects over the entire body.

BACKGROUND OF THE INVENTION

The concept of a slow release insecticide is known in the art. Typically, insecticides are formed into plastic ear tags or the like which are then attached to the animal's ear. As the plasticizer in the plastic ear tag gradually leaches out, it also gradually leaches out the insecticide.

The advantage of insecticide ear tags are that they provide relief from insects particularly horn flys and face flys for an extended period of time.

Still other insecticides are applied directly to the animal's body through a spray. These insecticides are of short duration, usually only a few hours.

Still other insecticides are applied directly to the animal's body through an insecticide-soaked bar that the animals rub against.

The present invention provides a slow release insecticide through application of a gellable liquid containing an in situ insecticide to a localized area on the animal. After application, the liquid composition congeals and forms a bead with in situ insecticide. Through a mechanism not fully understood it is believed that the bead gradually erodes away releasing the in situ insecticide in sufficient quantities to kill insects on the animal such as face flys and horn flys for an extended period of time.

SUMMARY OF THE INVENTION

The present invention is directed to the discovery of a composition comprising a cellulosic film former (typically hydroxypropyl cellulose) and an in situ insecticide and a liquid vehicle including a volatile alcohol. The gellable composition when applied to an animal's body through a squeeze bottle or the like leaves a rapidly drying bead of liquid on the animal that quickly congeals to leave a dry-to-the-touch bead or film with in situ insecticide that has been found to be released in effective insect killing quantities over an extended period of time.

DESCRIPTION OF THE PREFERRED EMBODIMENT

The in situ insecticide of the present invention is a liquid at room temperature which can be directly poured or squeezed in a liquid stream onto a portion of an animal's body. Generally, the liquid solution is squeezed as an extended bead along the animal's back or neck. As the liquid vehicle in the solution evaporates, the solution congeals to form a dry-to-the-touch bead on the animal's body. In order to kill insects a synthetic pyrethroid insecticide such as permethrin is incorporated into the solution prior to applying the solution to the animal's body. The mechanism of insecticide release is not fully understood but it has been found that an insecticide when encapsulated in the gel is released in effective quantities over an extended period of time to control insects on the body of the animal.

In the in situ insecticide the combination of the insecticide and gel are sufficient to provide extended relief from insects; however, to increase the length of effectiveness one can incorporate a microporous powder into the gel to provide multiple sites or reservoirs for additional insecticide. Also, to increase the effectiveness in killing other insects, other synergistic material can be added to the insecticide to increase the effectiveness.

The following is an example of the combination of the gellable liquid and an insecticide to produce extended relief from insects for up to three weeks or more.

EXAMPLE I

In preparation of the liquid insecticide of the present invention one mixes at room temperature 15 parts by weight of hydroxypropyl cellulose, 65 parts by weight of alcohol and 20 parts by weight of the insecticide permethrin. After mixing the liquid insecticide was applied in a liquid bead directly to the back of the animal. As the solvent evaporated, it left a dry-to-the-touch bead that adhered to the body hairs of the animal. The animal was allowed to remain in an outside environment as the effectiveness of the insecticide was periodically checked. After three weeks the in situ insecticide was found to still be effective in killing insects on the animal.

The amount of in situ insecticide may vary depending on the concentration of the insecticide and the amount of insecticide required for killing insects. Generally, there should be sufficient quantity of insecticide so that effective quantities of insecticide are released over an extended period of time. When permethrin is used alone, I have found that quantities as low as 2% by weight are sufficient to provide insect killing quantities for up to three weeks or more. Preferably concentrations of 1% to 10% are used. Higher or lower concentrations can be used in some cases. Measured in terms of each animal, one should generally apply at least 0.2 grams of permethrin per kilogram of body weight of the animal. However, it should be understood that such amounts may vary due to the tolerance that insects may develop to the insecticide.

Various animals may be treated using the method and compositions of the present invention including cattle, sheep, pigs, goats, horses and the like.

Generally, the synthetic pyrethroids such as permethrin and cypermethrin have been found to provide excellent results. Other insecticides sold under names such as Fenvalerate, Decamethrin, Flucythrinate, Alphametrin, Bendiocarb and Delnav are suitable. In fact, any insecticides which do not contain any ingredients that react with the gel are suitable for use. It will also be necessary to select insecticides which are nontoxic to the animal species to be protected from insects in the formulation chosen. A partial list of insecticides suitable for use is as follows: 2,2-Dimethyl-1,3-benzodioxol-4-yl methylcarbamate (Ficambendiocarb); ($\pm$) alpha-cyano-3-phenoxybenzyl($\pm$) cis.trans 3-(2,2-dichlorovinyl)-2,2-dimethyl cyclopropane-carboxylate (Cypermethrin); (s)-alpha-Cyano-M-phenoxybenzyl (1R,3R)-3-(2, 2-dibromovinyl)-2,2-dimethyl cyclopropane-carboxylate (Decamathrin); 2,3-p-Dioxanedithiol-S,S-bis(0,0- diethyl phosphorodithioate) (Delnav); Cyano(3-phenoxyphenyl)methyl-4-chloro alpha (1-methylethyl) benzeneacetate (Fenvalerate); (±) - cyano (3-phenoxyphenyl) methyl (±)-4-(difluromethoxy) alpha-(1-methylethyl) benzene acetate (Flucythrinate); and (3-phenoxyphenyl)-methyl (+or −) cis-trans-3-(2,2-dichloroethenyl)-2,2) dimethylcyclopropane-carboxylate (Permethrin).

In order to increase the susceptibility of insects to the in situ insecticide I can use an additive such as either piperonyl butoxide or N,N- di(2,4-xylyliminomethyl)-methylamine, preferably in amounts ranging in the ratio of one part additive for each four parts of insecticide to ten parts additive for each one part of insecticide.

Examples of the preparation of the solution of the present invention using an additive and a microporous powder to provide multiple sites or reservoirs of an insecticide are as follows:

EXAMPLE 2

First, a sufficient amount of 200 micron low density powdered polypropylene is added to 10 parts by weight of liquid piperonyl butoxide until the piperonyl butoxide is absorbed by the powdered polypropylene. The mixture of piperonyl butoxide and powdered polypropylene which is at a temperature of 100° F. is set aside.

Next, a sufficient amount of 200 micron low density polypropylene is added to 10 parts by weight of liquid permethrin until the liquid permethrin is absorbed by the powdered polypropylene to form a batch of permethrin and polypropylene. This batch of liquid permethrin and powdered polypropylene which was also mixed at 100° F. is then set aside.

Next, 15 parts by weight of hydroxypropyl cellulose and 65 parts by weight of isopropyl alcohol are mixed at a temperature of about 100° F.

In the final step the three batches of material are mixed together providing an extended life insecticide. Although liquid, the mixture exhibited thixotropy and had characteristics of a light gel solution.

The liquid insecticide was placed into a squeeze bottle for application directly to an animal. To test the effectiveness of the insecticide, the liquid insecticide was squeezed directly from the bottle onto the back of an animal thereby leaving a bead of liquid insecticide solution on the animal. In a few seconds the alcohol in the liquid insecticide evaporated leaving a continuous dry-to-the-touch bead of gelled insecticide on the animal. The gelled insecticide remained effective in killing insects on the animal for up to six weeks or more. During the test period it was noted that there was significant control of stable flys, houseflys, horn flys and ticks.

It should be understood that the alcohol provides a rapid evaporation solvent that allows the hydroxypropyl cellulose to quickly congeal. Any water in the liquid insecticide functions to dilute the cellulose material into a light, pourable gel form as well as acting as a carrier to disperse insoluble material throughout the mixture.

The liquid vehicle in which the insecticide, the microporous powder and the water soluble cellulose derived film-former is employed preferably includes from about 80% to about 100% by weight of volatile alcohol. Although alcohols are the preferred organic volatile solvent, any solvent which is volatile, nontoxic and a solvent for the other ingredients may be used, for example ketones such as acetone, methyl ethyl ketone and the like and esters such as ethyl acetate. The liquid vehicle may include quantities of water ranging from very small amounts up to about 50% by weight of the liquid vehicle. When applied to an animal, the volatile, low-boiling alcohol constituent evaporates readily leaving a bead on the animals back. If significant quantities of water, for example 50% by weight of the liquid vehicle, are incorporated in the liquid vehicle, then the drying appears to proceed in two stages, first the majority of the volatile alcohol moiety evaporates leaving a soft, tacky residual gel bead, secondly, somewhat more lengthy drying of the gel renders the gel substantially dry to the touch. If, on the other hand, the vehicle comprises primarily a volatile alcohol such as isopropanol (at least about 70% by weight), then upon evaporation of the alcohol portion of the liquid vehicle the gel becomes substantially dry to the touch even though it may contain a substantial quantity of water. In one embodiment in which substantially the entire liquid vehicle is volatile alcohol, evaporation of the vehicle from the coating occurs quickly, within about five minutes, and the resulting coating is dry to the touch and is soft and pliable. It is believed that the gel absorbs some water from the air. Preferably, the liquid vehicle includes a sufficient concentration of volatile alcohol so that when the alcohol moiety evaporates, the gel is rendered substantially dry to the touch.

The composition of the invention generally takes the form of a lightly viscous, pourable liquid. It is believed that some light gel formation occurs due to the presence of the cellulosic film-former. Of interest, higher temperatures appear to increase rather than decrease the viscosity of the composition. Accordingly, when the composition is applied to the animal's hide, the composition tends to solidify on the animal rather quickly. The viscosity of the pour-on insecticide can be controlled through judicious selection of type and quantity of cellulosic film former, and also through the addition of various thickening agents such as fumed silica, e.g., Cab-O-Sil, a product of Cabot Chemical Company.

Under most conditions the preferred range of the film-forming, water soluble cellulosic material, typically, hydroxypropyl cellulose, in the solution varies from a minimum of approximately 0.5% by weight to a maximum of approximately 25% by weight depending on the thickness of the coating desired. If the concentration of hydroxypropyl cellulose is very low, it produces a wider, thinner bead. On the other hand, if the mixture is too thick, it is difficult to apply to the animal's hide since it is believed that in the less viscous form the liquid cannot flow around the hairs on the animal before it congeals. Thus, the range of hydroxypropyl cellulose has as its limit the practical range at which it can be applied to the animal which may vary under various environmental conditions. However, it has been found that the preferred amount of hydroxypropyl cellulose for most applications ranges from a minimum of 0.5% by weight to a maximum of 20% by weight. Under most conditions a solution of approximately 1% by weight produces a film of sufficient durability to last up to three weeks or more.

The amounts of the insecticide are such that they would be effective over at least a three-week period. While more or less insecticide can be used, the preferred range of permethrin as the insecticide is a maximum of approximately 10% by weight. It should be understood that other insecticides may be used at greater or lesser concentrations; however, it has been found that permethrin in combination with piperonyl butoxide is ideally suited since it provides insect killing potential of up to six weeks or more. If desired, the hydroxypropyl cellulose can be used without the piperonyl butoxide. While hydroxypropyl cellulose is the preferred material, other cellulosic film formers such as ethyl cellulose or methyl cellulose may also be used. Mixtures of cellulosic film formers may be used. While the preferred embodiment comprises applying the insecticide directly on the animal, the liquid could also be applied to a container fastened to the animal's halter or the like.

The microporous polymers for use in the invention are known in the art and are commercially available. One such method of making microporous polymers is shown in U.S. Pat. No. 4,247,498.

Other conventional formulation ingredients can be added to the formulations of the invention in relatively small amounts to aid in processing or to increase stability. Antioxidants such as butylated hydroxyanisole (BHA), butylated hydroxytolvene (BHT) and the like may be used, preferably in amounts ranging from 0.01 to 1.0%. Other stabilizers such as compounds which protect against the deleterious effects of ultraviolet light can also be used in amounts from 0.01 to 1.0%. An example is Uvinul MS 40, available from BASF-Wyandotte.

To aid in processing, various ingredients such as defoaming agents can be added in amounts ranging from 0.01 to 1%.

The following example illustrates the use of various formulation ingredients in the invention.

EXAMPLE 3

To 74.1 pounds of isopropyl alcohol was added 0.6 pounds of hydroxypropyl cellulose (Klucel HF, Hercules Chemical Company, Wilmington, Del.) and 0.15 pounds of ethyl cellulose (Klucel EF, Hercules Chemical Company). Mixing was carried out for about eight hours, then the solution was allowed to stand for about 16 hours. To the solution was added 0.038 pounds of a defoaming agent (L45 Silicone 1000 Centastroke, Union Carbide Corporation, Danbury, Conn.), 0.075 pounds of an ultraviolet inhibitor (Uvinul MS40, BASF-Wyandotte, Wyandotte, Mich.) and 0.038 pounds of butylated hydroxyanisole antioxidant (Tenox BHA, Eastman Chemical Company, Rochester, N.Y.) and mixing was carried out over 45 minutes to provide the "base solution".

A 0.5 pound portion of polypropylene (Accurel, Armak, Chicago, Ill.) warmed to 130° F. was thoroughly mixed with 10 pounds of piperonyl butoxide at 130° F. Similarly, a 0.5 pound portion of polypropylene at 130° F. was mixed with 2 pounds of permethrin at 130° F.

The "base solution" and 12 pounds of isopropyl alcohol were mixed and heated to 130° F. To this solution was added both of the polypropylene mixtures and mixing was continued at 130° F. for about 30 minutes. The mixture was allowed to cool to ambient temperature and stored for use.

When applied to animals the formulation was found to provide good control of insects.

I claim:

1. A gellable slow release composition for killing organisms over an extended period of time comprising: a microporous polymer powder carrier providing multiple insecticide reservoirs, said insecticide reservoirs containing an insecticide, said microporous polymer powder and said insecticide reservoirs located in a liquid water soluble film former and a volatile alcohol to provide a gellable liquid to permit application to an animal for protection against organisms over an extended period of time, said gellable liquid comprises about 1 to 10 percent insecticide, about 0.5 to 20 percent film former and sufficient liquid vehicle to provide up to 98.5 percent of the gellable liquid.

2. The gellable slow release composition of claim 1 wherein the insecticide is selected from the group consisting of 2,2-dimethyl-1,3-benzodioxol-4-yl methylcarbamate; (±) alpha-cyano-3-phenoxybenzyl )±) cis, trans 3-(2,2-dichlorovinyl)-2,2-dimethyl cyclopropanecarboxylate; (s)-alpha-cyano-m-phenoxybenzyl (1R,3R)-3-(2,2-dibromovinyl)-2,2-dimethyl cyclopropanecarboxylate; 2,3-dioxanedithiol-S,S-bis(0,0-diethylphosphorodithioate); cyano(3-phenoxy-phenyl)-methyl 4-chloro-alpha-(1-methylethyl)benzeneacetate; (±) -cyano(3-phenoxyphenyl)methyl (±) -4-(difluoromethoxy) alpha-(1-methylethyl)benzeneacetate; and (3-phenoxyphenyl)methyl (±) cis, trans-3-(2,2-dichloroethenyl)-2,2-dimethylcyclopropanecarboxylate.

3. The gellable slow release composition of claim 1 wherein the film former is selected from one or more of ethyl cellulose, methyl cellulose and hydroxypropyl cellulose to provide a gellable liquid.

4. The gellable slow release composition of claim 1 wherein the volatile alcohol comprises isopropyl alcohol.

5. The gellable slow release composition of claim 1 wherein the microporous polymer powder comprises microporous polyproylene powder.

6. The composition of claim 1 including an additive selected from piperonyl butoxide and N,N-di(2,4,-xylyliminomethyl)methylamine.

7. The composition of claim 1 wherein the film former is hydroxypropyl cellulose.

* * * * *